United States Patent [19]

Burbank, III et al.

[11] Patent Number: 5,431,668
[45] Date of Patent: Jul. 11, 1995

[54] LIGATING CLIP APPLIER

[75] Inventors: John E. Burbank, III, Ridgefield, Conn.; John Pedlick, Butler, N.J.; David Stefanchik, Mason, Ohio; Jonathan Gabel, Highland Heights, Ky.; Thomas Petrella, Amelia, Ohio; Guy L. Osborne, Trumbull, Conn.

[73] Assignee: Ethicon, Inc., Somerville, N.J.

[21] Appl. No.: 54,734

[22] Filed: Apr. 29, 1993

[51] Int. Cl.⁶ .............................................. A61B 17/04
[52] U.S. Cl. ..................................... 606/143; 227/901
[58] Field of Search .............................. 606/142–143; 227/901, 902, 175–178, 181, 182

[56] References Cited

U.S. PATENT DOCUMENTS

| | | | |
|---|---|---|---|
| 3,777,538 | 12/1973 | Weatherly et al. | 72/410 |
| 3,870,048 | 3/1975 | Yoon | 128/326 |
| 3,955,581 | 5/1976 | Spasiano et al. | 128/334 R |
| 4,027,510 | 6/1977 | Hiltebrandt | 72/37 |
| 4,038,987 | 8/1977 | Komiya | 128/321 |
| 4,101,068 | 7/1978 | Buck | 229/35 |
| 4,152,920 | 5/1979 | Green | 72/410 |
| 4,166,466 | 9/1979 | Jarvik | 128/325 |
| 4,169,476 | 10/1979 | Hiltebrandt | 128/325 |
| 4,185,762 | 1/1980 | Froehlich | 227/138 |
| 4,196,836 | 4/1980 | Becht | 227/110 |
| 4,226,239 | 10/1980 | Polk et al. | 128/303 A |
| 4,226,242 | 10/1980 | Jarvik | 128/325 |
| 4,230,116 | 10/1980 | Watson | 128/303 A |
| 4,242,902 | 1/1981 | Green | 72/410 |
| 4,246,903 | 1/1981 | Larkin | 128/325 |
| 4,273,129 | 6/1981 | Boebel | 128/326 |
| 4,296,751 | 10/1981 | Blake, III et al. | 128/325 |
| 4,299,224 | 11/1981 | Noiles | 128/325 |
| 4,316,468 | 2/1982 | Klieman et al. | 128/325 |
| 4,325,376 | 4/1982 | Klieman et al. | 128/325 |
| 4,372,316 | 2/1983 | Blake, III et al. | 128/325 |
| 4,374,523 | 2/1983 | Yoon | 128/326 |
| 4,412,539 | 11/1983 | Jarvik | 128/325 |
| 4,425,915 | 1/1984 | Ivanov | 128/325 |
| 4,430,997 | 2/1984 | DiGiovanni et al. | 128/326 |
| 4,452,357 | 6/1984 | Klieman et al. | 206/339 |
| 4,452,376 | 6/1984 | Klieman et al. | 221/198 |
| 4,471,780 | 9/1984 | Menges et al. | 128/326 |
| 4,478,220 | 10/1984 | DiGiovanni et al. | 128/326 |
| 4,480,641 | 11/1984 | Failla et al. | 128/326 |
| 4,509,518 | 4/1985 | McGarry et al. | 128/325 |
| 4,522,207 | 6/1985 | Klieman et al. | 128/325 |
| 4,534,351 | 8/1985 | Rothfuss et al. | 128/334 R |

(List continued on next page.)

FOREIGN PATENT DOCUMENTS

| | | |
|---|---|---|
| 0068046 | 1/1983 | European Pat. Off. |
| 0409569 | 1/1994 | European Pat. Off. |
| WO 900376 | 4/1990 | France |

Primary Examiner—Gary Jackson
Attorney, Agent, or Firm—Paul A. Coletti

[57] ABSTRACT

There is described herein a ligating clip applier which contains: a handle assembly; a jaw assembly connected to the handle assembly and containing a shaft and a pair of jaws. The shaft defines a longitudinal axis which lies in a central horizontal plane. A magazine of clips is stored on one side of the plane. The jaws are positioned so that they are on the opposite side of the plane. This configuration allows the clip to be loaded into the jaws across the plane, resulting in greater visibility of the clips as they are loaded into the jaws. Further, there is provided a jaw closure mechanism operable in connection with the jaws of this device so that the jaws contact the legs of a ligating clip first distally and then proximally. Thereafter the jaws are parallel at least once during closure, and the closure of the clip legs is, indeed, distal and then proximal. This improved procedure insures that in virtually all instances, the angle included between the clip legs at the crown is 0°. Motion of the clip feeding and jaw closing mechanisms are accomplished without lost motion, via a pair of interengaged mechanisms connected by a single tension spring to one another, and operating separately from the body of the device. This configuration results in a more efficient, easier to operate more reliable clip applying device.

18 Claims, 9 Drawing Sheets

U.S. PATENT DOCUMENTS

| | | | |
|---|---|---|---|
| 4,549,544 | 10/1985 | Favaron | 128/335 |
| 4,565,199 | 1/1986 | Becht | 128/325 |
| 4,572,183 | 2/1986 | Juska | 128/325 |
| 4,576,166 | 3/1986 | Montgomery et al. | 128/325 |
| 4,598,711 | 7/1986 | Deniega | 128/326 |
| 4,611,595 | 9/1986 | Klieman et al. | 128/334 R |
| 4,616,650 | 10/1986 | Green et al. | 128/325 |
| 4,624,254 | 11/1986 | McGarry et al. | 128/325 |
| 4,646,740 | 3/1987 | Peters et al. | 128/325 |
| 4,662,373 | 5/1987 | Montgomery et al. | 128/325 |
| 4,674,504 | 6/1987 | Klieman et al. | 128/325 |
| 4,691,853 | 9/1987 | Storace | 227/19 |
| 4,712,549 | 12/1987 | Peters et al. | 72/410 |
| 4,784,137 | 11/1988 | Kulik et al. | 128/334 R |
| 4,841,888 | 6/1989 | Mills et al. | 112/169 |
| 4,850,355 | 7/1989 | Brooks et al. | 128/325 |
| 4,944,443 | 7/1990 | Oddsen et al. | 227/19 |
| 5,030,226 | 7/1991 | Green et al. | 606/158 |
| 5,049,152 | 9/1991 | Simon et al. | 602/143 |
| 5,084,057 | 1/1992 | Green et al. | 606/142 |
| 5,100,418 | 3/1992 | Yoon et al. | 606/139 |
| 5,100,420 | 3/1992 | Green et al. | 606/143 |
| 5,104,395 | 4/1992 | Thornton et al. | 606/143 |
| 5,112,343 | 5/1992 | Thornton | 606/143 |

LIGATING CLIP APPLIER

FIELD OF THE INVENTION

Generally, this invention relates to ligating clip appliers capable of performing the crushing of the legs of a metallic ligating clip between the jaws of the device, in order that the ligating clip may either ligate and occlude a blood vessel or other lumen, or approximate tissue.

BACKGROUND OF THE INVENTION

Ligating clip appliers or applicators have become quite common in the operating room. These appliers are generally able to engage a ligating clip between a pair of opposed jaws. Thereafter, the jaws crush the clip by applying a lateral pressure thereto. The clip is placed around a blood vessel to occlude or ligate the vessel, or alternately, the clip may be used to approximate severed tissue. Clip appliers may engage and clamp a single clip (and thereafter be reloaded), apply multiple clips simultaneously, or multiple clips seriatim, from a stack of clips held in a clip magazine on the clip applier. Exemplary clip appliers of each type are disclosed in an Information Disclosure Statement filed herewith.

Certain clip appliers which may be considered "automatic" are disclosed in the art, and for purposes of distinguishing with the invention claimed in this application, are discussed herein. Each of these devices has a pusher bar (for loading clips) and a camming channel (for closing clips) which move in opposite directions of one another, in order to provide more efficient clip closure and loading between the jaws. For instance, Deniega, U.S. Pat. No. 4,598,711 presents a clip applying device wherein a mechanism for loading clips is moved proximally while a separate mechanism for closing clips is moved distally, to close a clip between a pair of jaws. Then, these motions are reversed, in order to load a new clip between the pair of jaws. But, in Deniega, there are certain perceived drawbacks. First, the respective loading and closing mechanisms are operated in conjunction with a series of links and gears. These mechanisms require precise interaction of moving members, and are perceived as relatively cumbersome to operate properly. Second, a single tension spring controls the mechanism, to reverse the motion of the loading and closing operations, but this spring is attached to the housing of the device. In contrast, it would be desirable to employ an improved spring system which would not require special attachment to, or interaction with, the housing. Such a design could be more easily manufactured. Further, it would be advantageous to provide such improved spring system that could be operated more easily, more quickly, and more reliably.

Alternately, another mechanism which functions quite similarly to the Deniega patent is described in Green et al., U.S. Pat. Nos. 5,030,226 and 5,197,970. Here, the pusher bar (for loading clips) and camming assembly (for closing the jaws) are controlled not by one tension spring, but by a series of compression springs. Moreover, there are a pair of lever links attaching the pusher bar to the handles which operate the device. Also, the lever links slide within the handle of the device. Both the existence of the compression springs and the multiple lever links result in a device which necessarily requires a great deal of mechanical force to activate, as well as an offsetting movement resulting from the use of multiple lever links. Consequently, much energy must be used to overcome the friction resulting from the operation of the multiple links and the multiple compression springs. In addition, further amounts of energy are required to guide the pusher bar assembly, as it is connected to a pair of guide pins which are conducted through a pair of guiding channels located in the handles of the device. Again, the resultant energy and frictional losses create a device which is less than optimally efficient.

Furthermore, the Green device presents a mechanism which requires a certain amount of lost motion to be overcome in order to time and coordinate the motion of the pusher bar and the jaw camming assembly. In other words, there is no direct coordinated translation between motion of the handles to activate the device and motion of the pusher bar and jaw camming assemblies. This resultant lost motion requires yet additional force to be expended (over a resultantly lengthened period of activation time) in contrast to what would be considered an optional device.

Yet another "automatic" device are those endoscopic clip applying mechanisms described in Stefanchik et al. U.S. Pat. Nos. 5,171,249 and Hughett et al., 5,171,247. There, one tension spring activates the entire mechanism. Also, the spring is connected between the pusher bar and camming assemblies, and not between one assembly and the handle, as in the aforementioned Deniega and Green patents. This connection and the interaction of the two assemblies removes any lost motion from the operation of the device. Further, the clip appliers described in the Stefanchik et al. and Hughett et al. patents employ a single trigger actuator which is directly connected to the jaw closure mechanism and which is connected through a single, pivotably mounted link to the pusher bar mechanism. A special guide channel is provided in the body handle for guiding one end of the link as it moves the pusher bar mechanism proximally during operation of the trigger. Because this could result in added frictional losses in the system, it would be desirable to provide an improved system with less friction loss and with a less complex component design.

Finally, the clip appliers disclosed in the Stefanchik et al. and Hughett et al. patents are specially designed for use in endoscopic surgery with single trigger action wherein the trigger is directly connected to the jaw closure channel mechanism. This is highly effective and desirable in endoscopic procedures. However, in some applications, particularly in some types of open surgery procedures, a surgeon may prefer to employ a clip applier having a pair of handles. Indeed, in such applications it would be desirable to provide a clip applier with a pair of handles for operating the jaw closure mechanism through an appropriate linkage system to provide the surgeon with the feel of a traditional scissors type action.

Heretofore, there also have been certain other perceived drawbacks noted in conventional, "open" procedure multiple clip applying mechanisms. First, the jaws of the clip applier are traditionally positioned on and angled toward the same side as the magazine of clips with respect to a central dividing plane which lies along the longitudinal axis defining the shaft of the ligating clip applier. This has resulted in the clips necessarily being fed into jaws from the "underside" of the jaws, as the jaws of such clip applier are generally configured to angle in a direction apart from the dividing plane but toward the magazine of clips.

Second, the jaws of previous clip appliers have been configured so that they approximate and clamp the clip. There has been no emphasis on the method of jaw/clip closure. That is, heretofore, all the previous methods of jaw closure have relied on mere approximation of the jaws. Until now there has not been a careful designing of the jaws and the manner in which they approximate clips so that there is first a distal closure of the jaw legs, and then a gentle proximally moving closure of these jaw legs, so that the jaw closing force is concentrated on different points on the clip as the jaws flex and roll over the clip, so that the included distal angle of the clip legs at the crown of the clips is substantially 0°.

Third, the locking mechanisms which provide a locking of the jaw approximating mechanism have been simple barrier devices, but, at the same time, have been bulky in size with respect to the jaw approximating device itself. There has not been improvement of the lockout mechanism in size or performance capabilities.

SUMMARY OF THE INVENTION

Problems associated with the "automatic" clip appliers are overcome by the present invention. There is described herein a clip applying device containing a pair of jaws operated by a clip closing channel and a mechanism for loading clips into the jaws operated by a feed bar. The clip closing channel and feed bar are connected to a clip closing bar and a clip feed member, respectively. The clip closing bar and clip feed member are each connected via a pair of operating handles by a pair of pivoting levers. Also, the clip closing bar and the clip feed member are connected to one another by a single tension spring.

Motion of the handles toward one another causes each of the levers to guide the clip feed member proximally and the clip closure bar distally, so that a clip may be squeezed between the jaws. Then, when the handles are released, a single tension spring releases the energy stored therein during handle closure, so that the clip feed member moves distally to load a clip and the clip closing member moves proximally to allow feeding of the clip between the jaws.

This operation is effected without multiple levers, lost motion or the guiding of any of the moving mechanisms by a guiding device located on the handle. Moreover, this operation is accomplished by a single tension spring connected between the members, and not to the handle. Thus, the operation of this mechanism is accomplished in fashion functionally and operationally different from any of the methods disclosed in the art. This operation is significantly more efficient, and results in an easier to operate, more reliable device.

The associated drawbacks of former clip appliers are also obviated by the present invention. There is described herein a ligating clip applier which contains: a handle assembly; a jaw assembly connected to the handle assembly and containing a shaft and a pair of jaws. The shaft defines a longitudinal axis which lies within a central horizontal bisecting plane. A magazine of clips is stored on one side of the longitudinal plane. The jaws are positioned so that they are on the opposite side of and angled away from the horizontal plane. This configuration allows the clip to be loaded into the jaws across the horizontal plane, resulting in greater visibility of the clips as they are loaded into the jaws and during clip closure.

In other words, the applicants have created a device wherein the plane which contains the clips (ready to be loaded between the jaws) is immediately adjacent the plane for closing the jaws. This type operation has heretofore not been realized for operation of a ligating clip applier-type mechanism. Such a configuration allows the jaws to be angled up to 30° away from the plane of the jaw closing mechanism, an angle previously not even considered by manufacturers of elongated tubular shaft clip appliers. This 30° angle gives such improved clip visibility to the user, that it enhances the utility of such a device. This configuration also enables the concentrated crown closing force to be located in, or very close to the jaw cam plane, thus keeping the jaw components from twisting.

Further, there is provided a jaw closure mechanism operable in connection with the jaws of this device so that the jaws contact the legs of a ligating clip first distally and then proximally (toward the crown of the clip). Thereafter the jaws are parallel at least once during closure, and the closure of the clip legs is, indeed, distal and then proximal. The jaws, in fact, roll past a position parallel to each other, so that forces on the clip are concentrated at the crown, to thereby form a permanent set of the metallic clip, and avoid clip springback. This improved procedure assures the user that in virtually all instances, the angle included between the clip legs at the crown of the clip is substantially 0°. This, in turn, causes the legs to be spread apart only where tissue is contacted, and not at the crown, so that there is substantially no gap at the crown, which could result in a loosely attached clip.

Finally, there is described herein a unique lockout mechanism formed from a thin metallic member held in place by the clips stored in the clip magazine. When the last of the clips has been loaded into the jaws to be clamped, the lockout mechanism proceeds to drop into the path of the clip feeding mechanism. When this blocking occurs, the jaw clamping mechanism is similarly held in place by a lockout spring in the handle which, on the next attempted cycle, acts on the clamping mechanism. Thus, rather than merely serving as a blocking means, this thin metallic piece forms a "wall" for the feeding mechanism, which can only be bypassed by overcoming the rather substantial shear strength of the metal. This configuration, therefore, allows the thin metallic lockout member to maintain a relatively small size, (compared to earlier versions of these lockout devices) and yet, because of its positioning, still capably perform the desired lockout functions.

This invention will be better understood by the following Description of the Drawings taken in conjunction with the Detailed Description of the Invention.

DETAILED DESCRIPTION OF THE INVENTION

Figure 1:
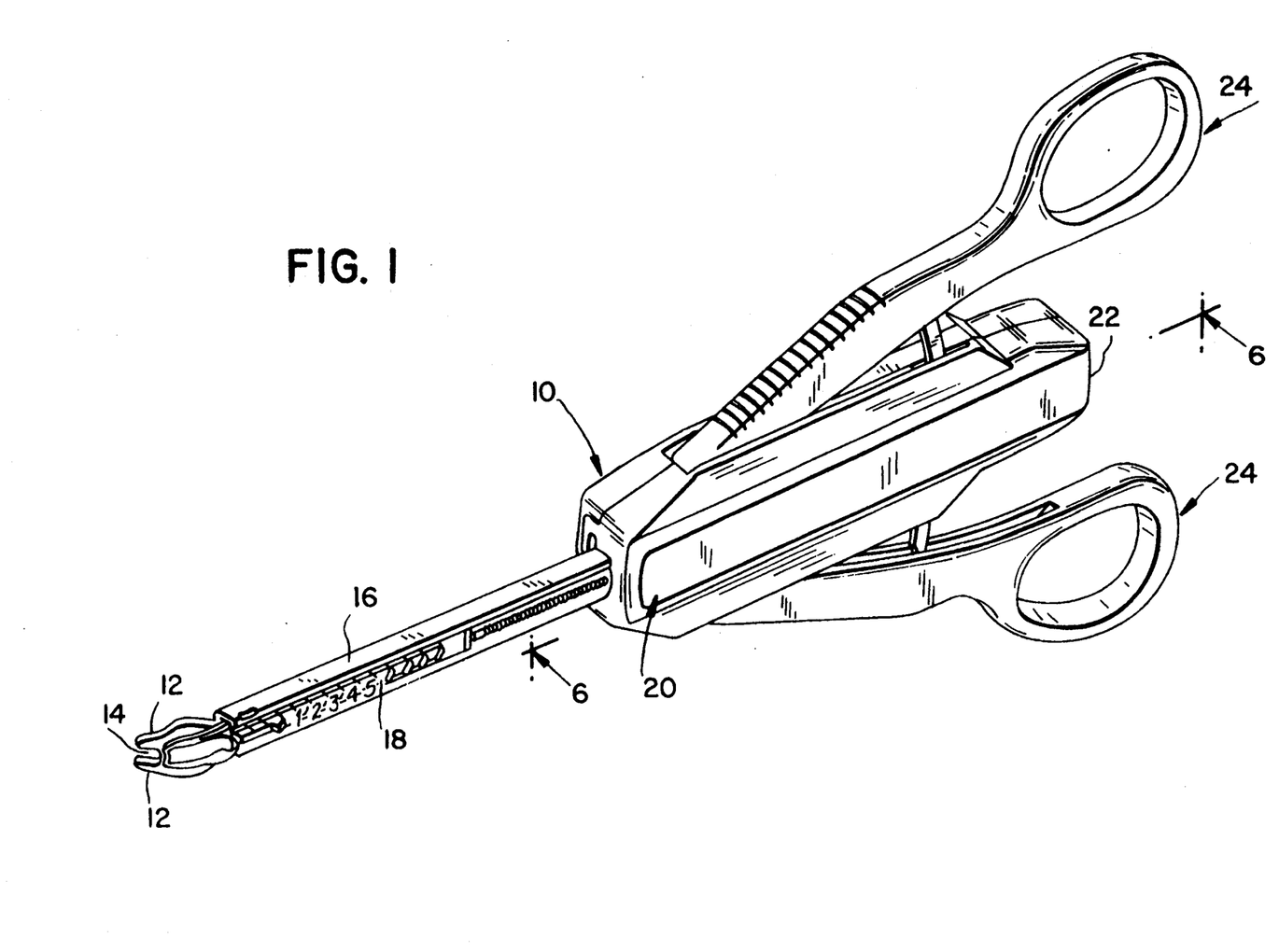
FIG. 1 is a perspective view of a ligating clip applier which forms this invention.

FIG. 1 shows a perspective view of a multiple clip applier 10 which describes this invention. As seen in FIG. 1 there are a pair of jaws 12 which are capable of holding a clip 14 therebetween. Also, as seen in FIG. 1, there is contained a shaft 16 of the mechanism 10 on which the jaws 12 are maintained. Shaft 16 has a longitudinal axis lying in a central horizontal plane of the mechanism. Jaws 12 are placed on one side of this plane. Cartridge magazine 18 is on the opposite side of this plane; jaws 12 angle away from the horizontal plane, at the above mentioned 30° angle to the horizontal plane. As can be better seen in connection with FIGS. 8–12 from cartridge 18, one of the clips 14 contained in the shaft 16 is to be fed into the pair of jaws 12 for clip closure. As better seen in FIGS. 3–7, the plane of cartridge 18 is immediately adjacent the plane containing the extensions of jaws 12, and parallel thereto.

The shaft 16 and the jaws 12 depend from the handle portion 20 of the mechanism 10. This handle portion 20 contains a body in which is held the clip closing mechanism which actuates the jaws and clip feeding mechanisms which helps supply clips 14 from along the shaft 18 of the mechanism between the jaws 12, as will be better described herein. Attached to the body 22 are a pair of ring handles 24. Each of these ring handles 24 is moved in scissors-like fashion in order to actuate each of the clip closing and feeding mechanisms of this invention.

As seen in FIGS. 1, 4, 6 and 7, the ring handles 24 are pivoted on holes 25 at pins 26 attached within the body 22 of the handle portion 20. Ring handles 24 are also attached at pins 28, 30 on varying positions along the body 22 to the hooks 31, 33 of a pair of lever arms 32, 34 held at a more proximal position along the shafts 36 of the ring handles. The ring handles 24 contain a pair of rings 38 capable of accepting two fingers of the same hand, in order to be squeezed close together, in order to thereafter actuate a clip 14 so that it is fed between the jaws 12 upon opening the handles 24, and to place the clip 14 and clamp it around a blood vessel or other tissue desired to be ligated or approximated.

Figure 2:
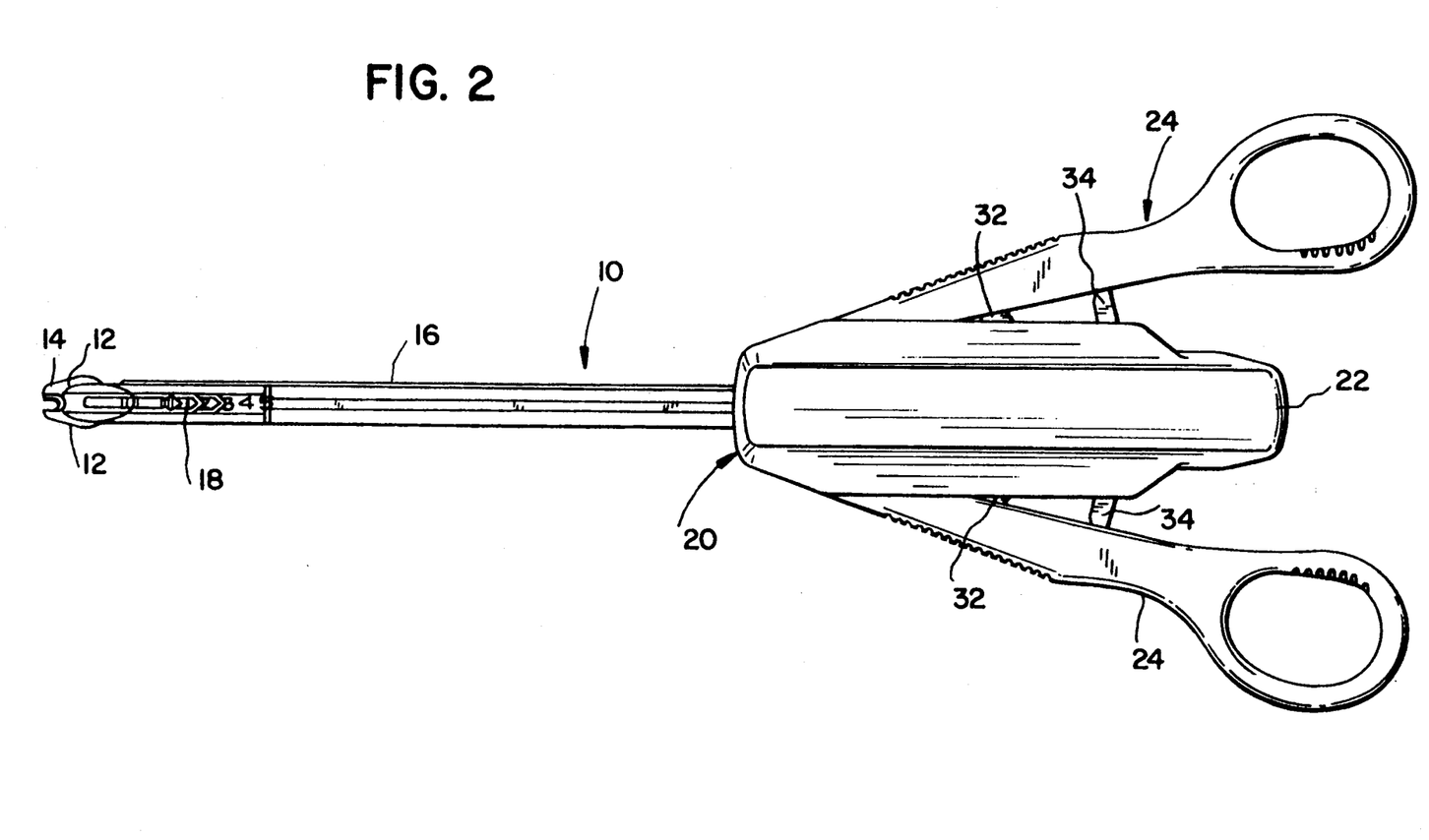
FIG. 2 is top view of the ligating clip applier of FIG. 1.

FIG. 2 shows the clip applier 10 in a elevation view, with a pair of jaws 12 holding a clip 14 therebetween, and the ring handles 24 held in a clip accepting position. As can be seen in FIG. 2, the distal pairs of lever arm 32 are in a clip accepting position, which causes the handles 24 to be spaced apart; the second proximally positioned pair of lever arms 34 is similarly also placed in a clip accepting position. These pairs of levers 32,34 will be more closely described below. The pairs of single levers 32,34 is of course in contrast to the multiple levers described in, for instance, the Green patents cited in the Background section of this application.

Figure 3:
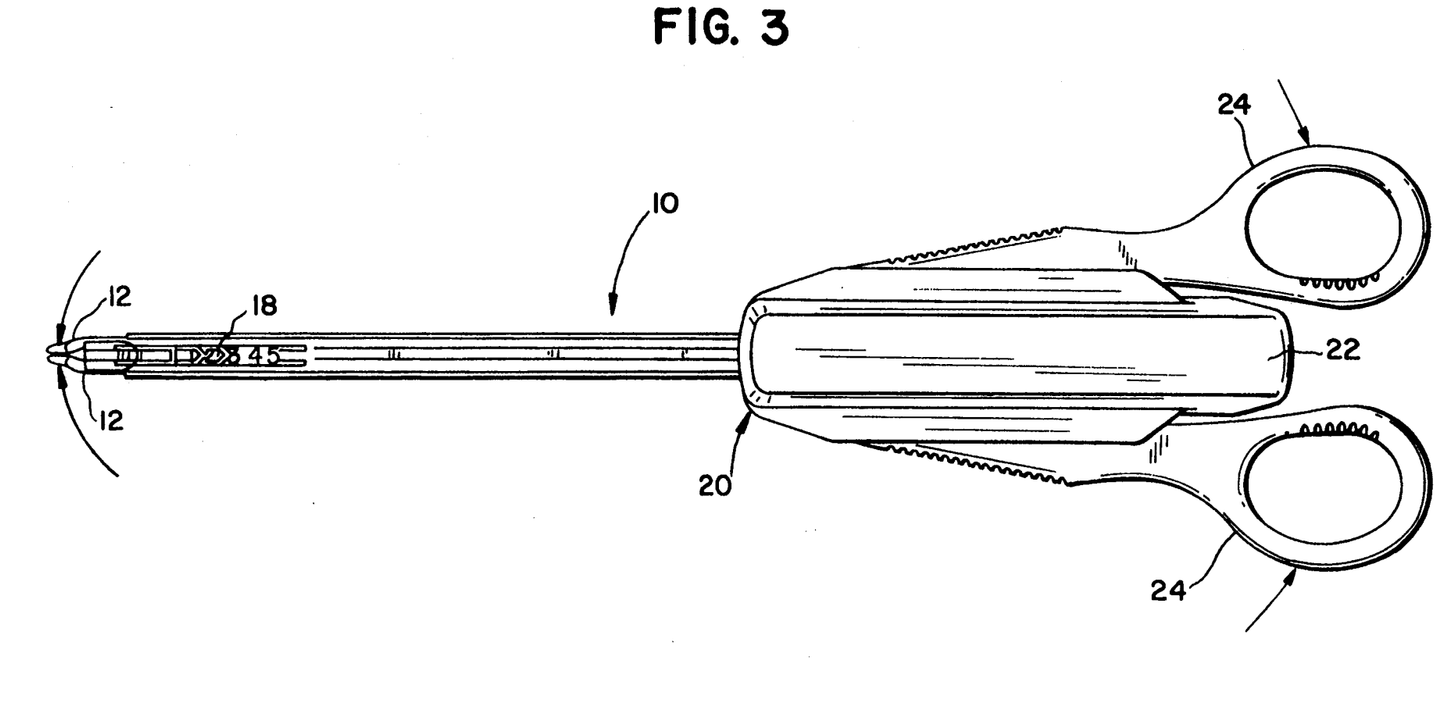
FIG. 3 is a view similar to that of FIG. 2 but with the jaws of the clip applier closed and the handles of the clip applier in a clamping position.

FIG. 3 shows the ring handles 24 when they have been approximated to a closed position toward the body 22 of the mechanism. Now, each of the distal and proximal pairs of levers 32,34 have moved to a clip closing position. When in this clip closing position, the jaws 12 of the mechanism 10 are caused to be closed one upon the other so that a clip 14 held between the jaws 12 is clamped about tissue. This is well disclosed in FIG. 3. After the clip 12 has been closed, the jaws 14 are caused by spring 40 (as seen in both of FIGS. 6 and 7) to open, thereby accepting another clip 14 delivered from the clip magazine 18. This will occur when the ring handles 24 are caused to move to their clip accepting position at the initiation of spring 40. In this fashion, the mechanism is recycled, and another clip 14 is capable of being occluded about tissue.

Figure 4:
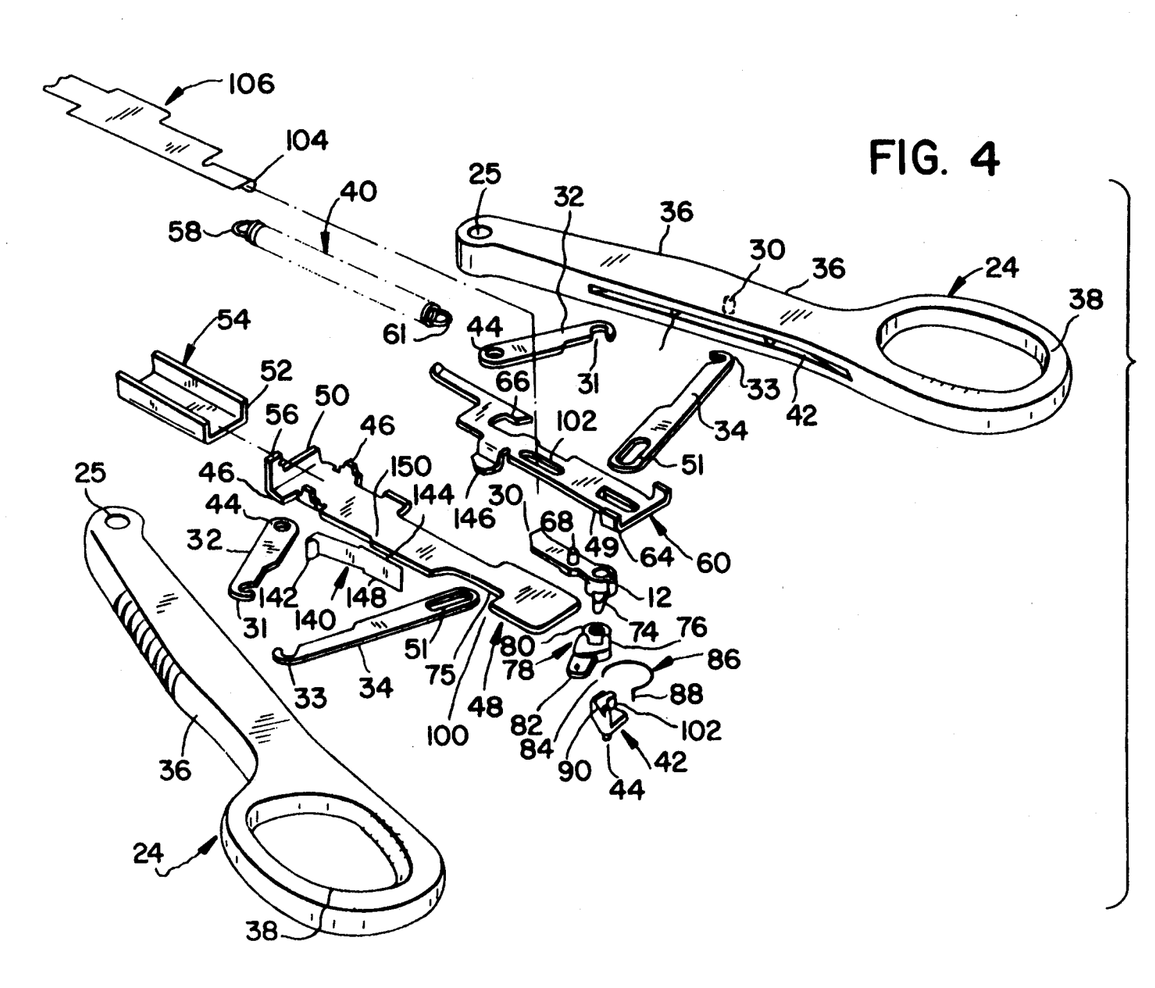
FIG. 4 is a perspective assembly view of the handle portion of the mechanism.

FIG. 4 shows a perspective assembly view of the mechanism held within the body 22 of the mechanism 10, in relation to ring handles 24. In essence, there are contained within body 22 a number of interacting mechanisms which enable the clip applier 10 to perform the clip closing and feeding functions as described herein. The mechanism as seen in FIG. 4 will be better understood in combination with the perspective view of FIG. 5. Thus, each of the ring handles 24 has attached to them one each of the pair of distal and proximal lever arms 32, 34, as already described. Each of these distal and proximal levers 32,34 is further attached to the internal, "working" portion of the instrument, embodied by the body 22 of the mechanism. The distal levers 32 are attached to the ring handles 24 at the pair of hooks 31, which are latched around the pins 28 contained in the slot 42 found in each of the ring handles 24. Thus, distal levers pivot at pins 28 of ring handles 24. Further, on their opposite ends, the distal levers 32 are attached at holes 44 to the posts 46 of the clip closing and timing bar 48. This allows distal levers 32 to pivot with respect to posts 46, so that the relative position of levers 32 and clip closing bar 48 changes during motion of ring handles 24.

Figure 5:
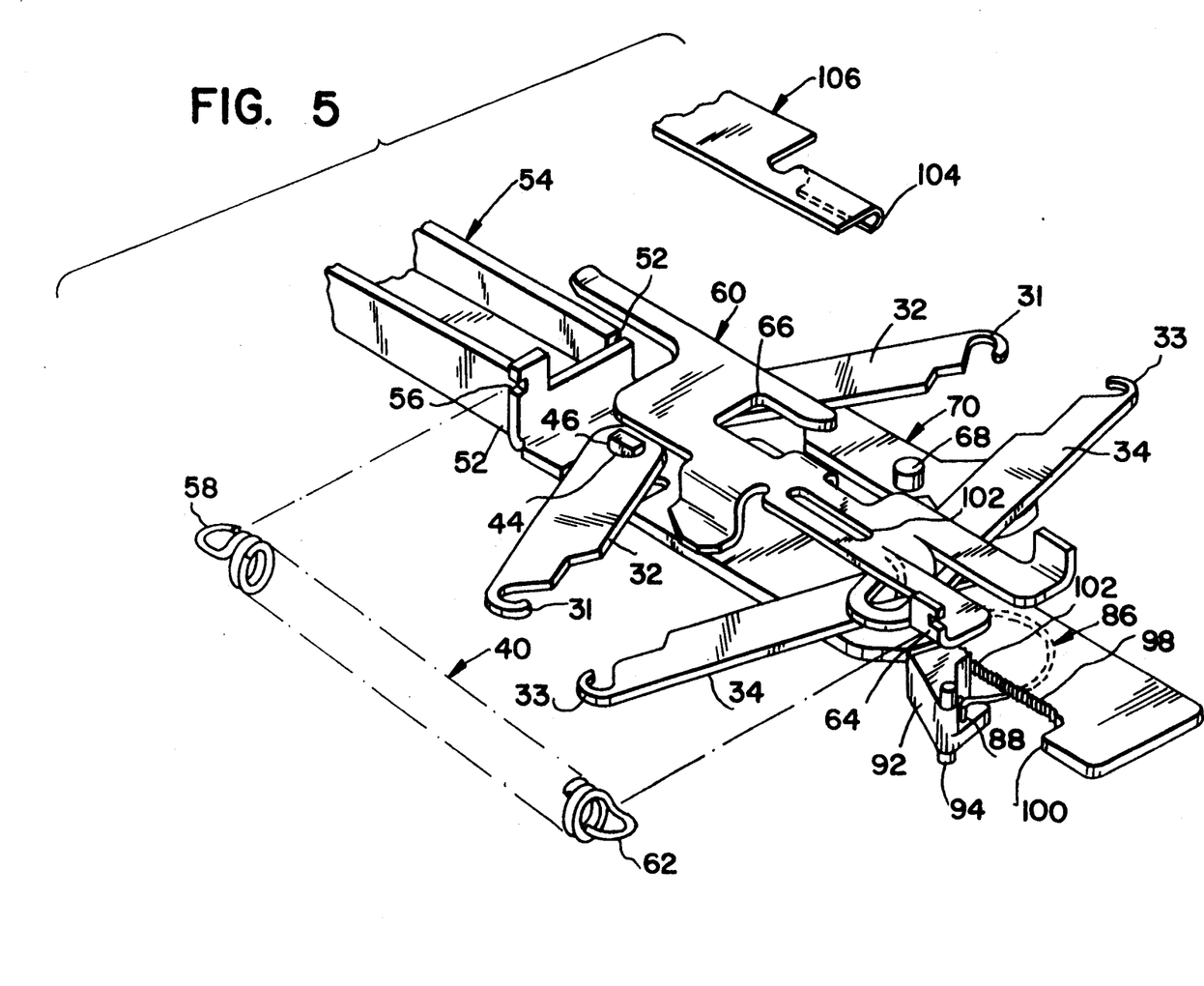
FIG. 5 is a perspective view of the moving pieces contained in the handle portion of the device.
Figure 6:
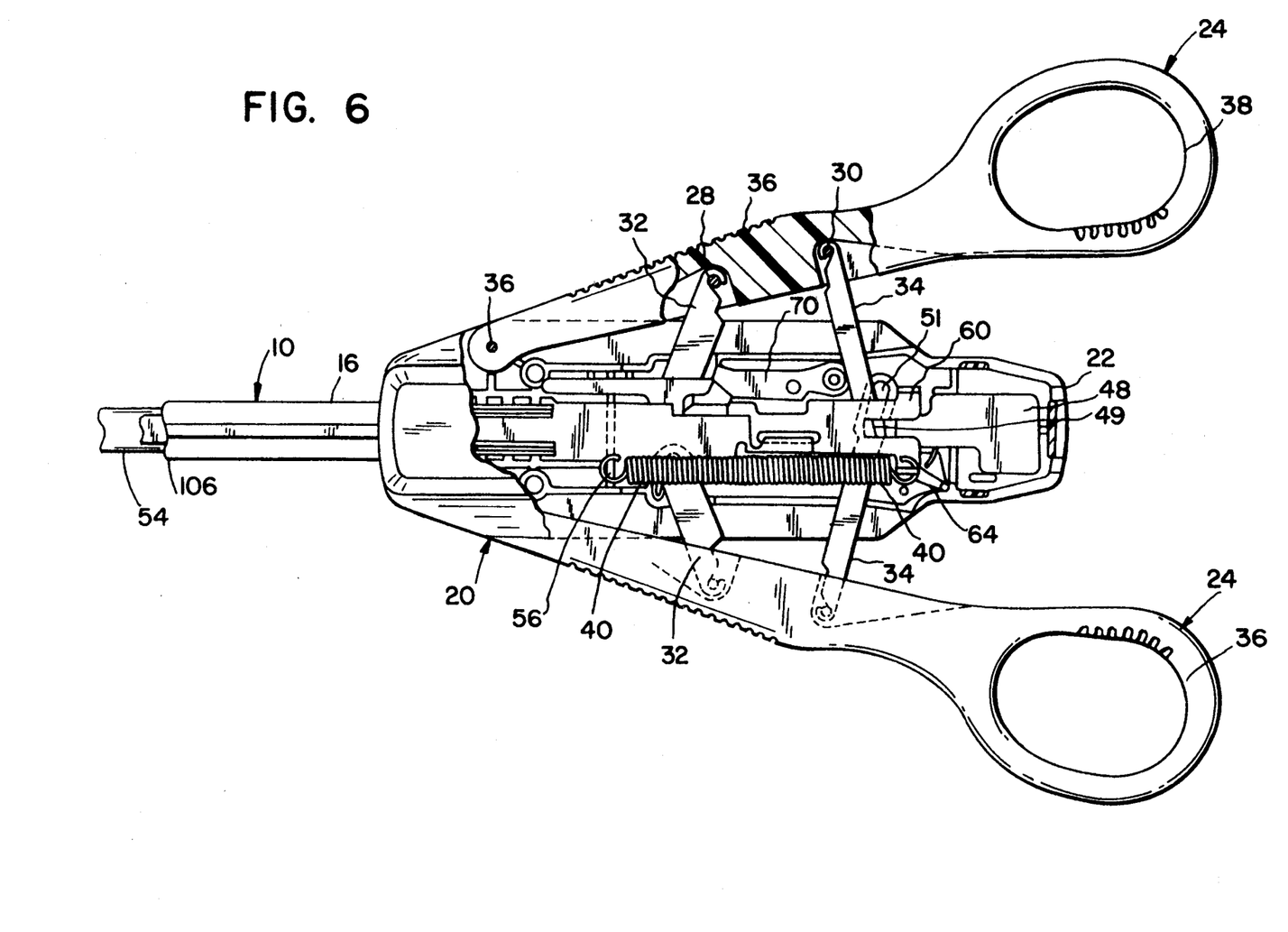
FIG. 6 is a partial cross-section of the handle portion of the mechanism taken across lines 6—6 of FIG. 1.
Figure 7:
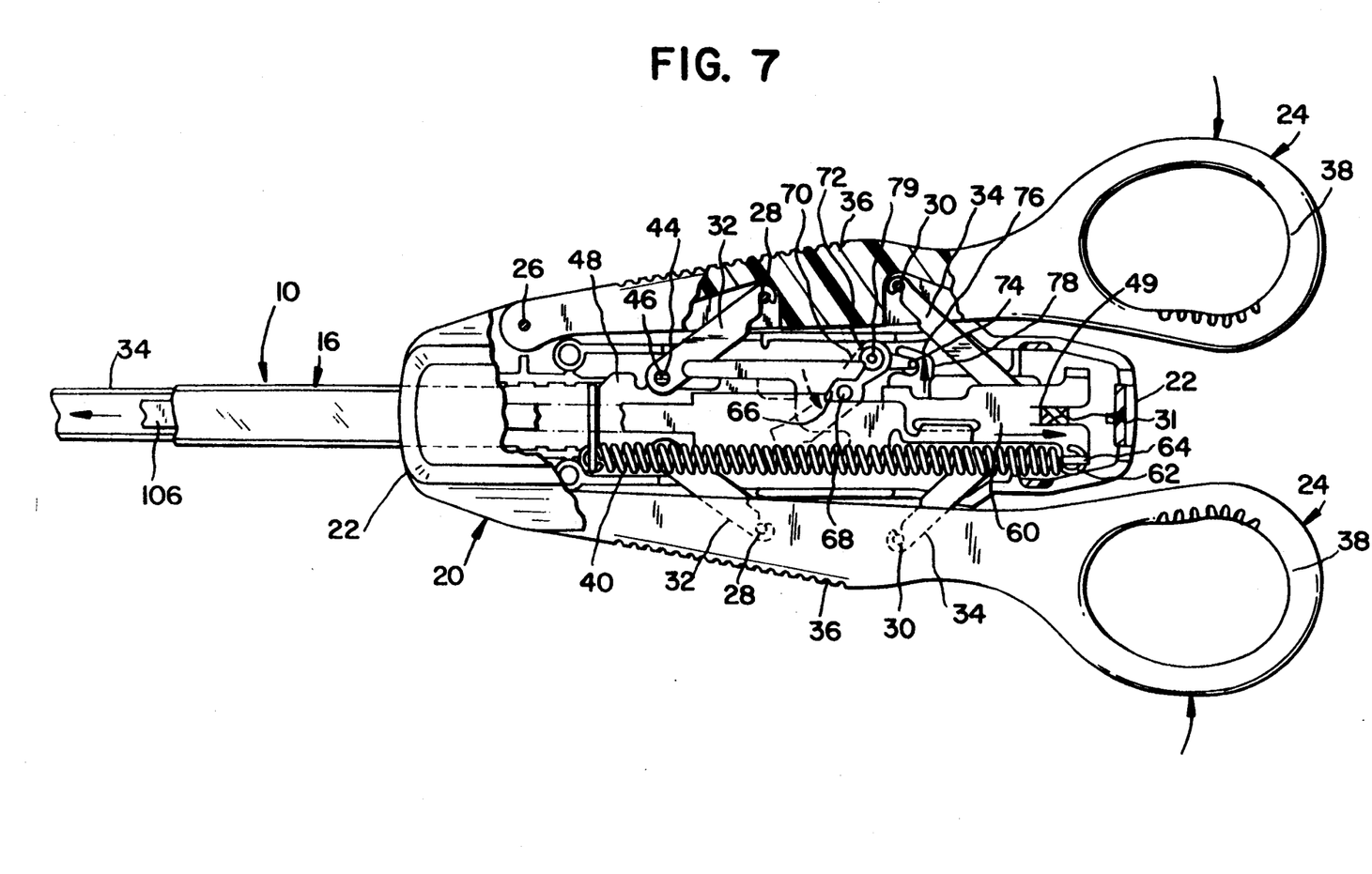
FIG. 7 is a view similar to that of FIG. 6, but with the handles in the position as seen in FIG. 3.

Hook 49 of clip feed member 60 slides in slots 51 of proximal levers 34, as seen in FIGS. 5, 6 and 7. Proximal levers 34 are also attached at hooks 33 to pins 30 of ring handles 24. In this fashion, proximal levers 34 behave during clip clamping in much the same (although mirror imaged) fashion as distal levers 32. Again, there are no guide pins or channels connecting these levers 32,34 or the clip feed member 60 or clip closing bar 48 to the handle 22, in a fashion similar to the above cited Stefanchik, Hughett or Green patents.

Further, the clip closing bar 48 is attached by a hook (not shown) at hook shaped end 50 to the proximal end 52 of clip closing channel 54 as seen in FIGS. 4 and 5. Optionally, there is also included at the connection between ends 50 and 52, an anti-backup spring (also not shown) which provides a force to the clip closing channel to prevent any backup of channel 54 during closure of the clips 12 should the user temporarily release his grip during the closing process. The anti-backup spring therefore reinforces the ratcheting mechanism used for clip closure.

The clip closing bar 48 is further attached to distal end 58 of spring 40 at notch 56, which holds the clip closing bar 48 in contact with the clip feeding member 60 through attachment at proximal end 62 to notch 64. This spring 40 causes the recycling of the mechanism 10 after firing. Spring 40 is a single tension spring, in contrast to the compression springs used in some of the previous clip applying devices, such as the Green devices cited above. This clip closing bar 48 will be later described in relation to its functions at the distal end of the shaft 16 of the mechanism 10.

As seen in FIG. 4, further received within the clip feed member 60 (at notch 66), is the post 68 of a timing member 70. Hole 72 causes timing member 70 to pivot about post 79 attached to body 22 (FIG. 7). Pawl 74 of timing member 70 fits into U-shaped prongs 76 of timing bar 78. This interrelationship causes timing bar 78 to similarly pivot about post 79 which holds bar 78 in place at hole 80. Distal end 84 of return spring 86 is attached to timing bar 78 at hole 82. Proximal end 88 of return spring 86 is attached to hole at notch 90 of pivot 92. Pivot 92 is connected at post 94 to the body 22. Ridges 96 of pivot 92 contact ridges 98 of clip closing bar 48, to give a ratcheting effect. Hook shaped end 100 of clip closing bar 48 contacts end 102 of pivot 92. This occurs during forward motion of clip closing bar 48. Such motion causes return spring 86 to pivot the timing bar 78, clockwise about hole 80 in a generally distal direction, which permits motion of timing member 70 clockwise out of the path of clip feed member 60. Such motion allows spring 40 to contract, allowing the motion of the drive mechanism from that of FIG. 7 to return to the position seen in that of FIG. 6. Such timing and cycling of the instrument is similar to that described in U.S. Pat. No. 5,171,249 incorporated herein by reference.

The clip feeding sequencing of the mechanism is actuated by the clip feeding member 60, which is connected to the pair of lever arms 34 as seen in FIGS. 4 and 5 and explained above. Clip feeding member is further connected at slot 102 to hook 104 of feed bar 106. Clip feeding member 60, because it is attached to the ring handles 24 via the proximal levers 34 is capable of causing a clip 14 to be loaded within the jaws 12 by actuating the feed bar 106, as will be seen in the sequence of FIGS. 8 through 12.

Figures 8, 9:
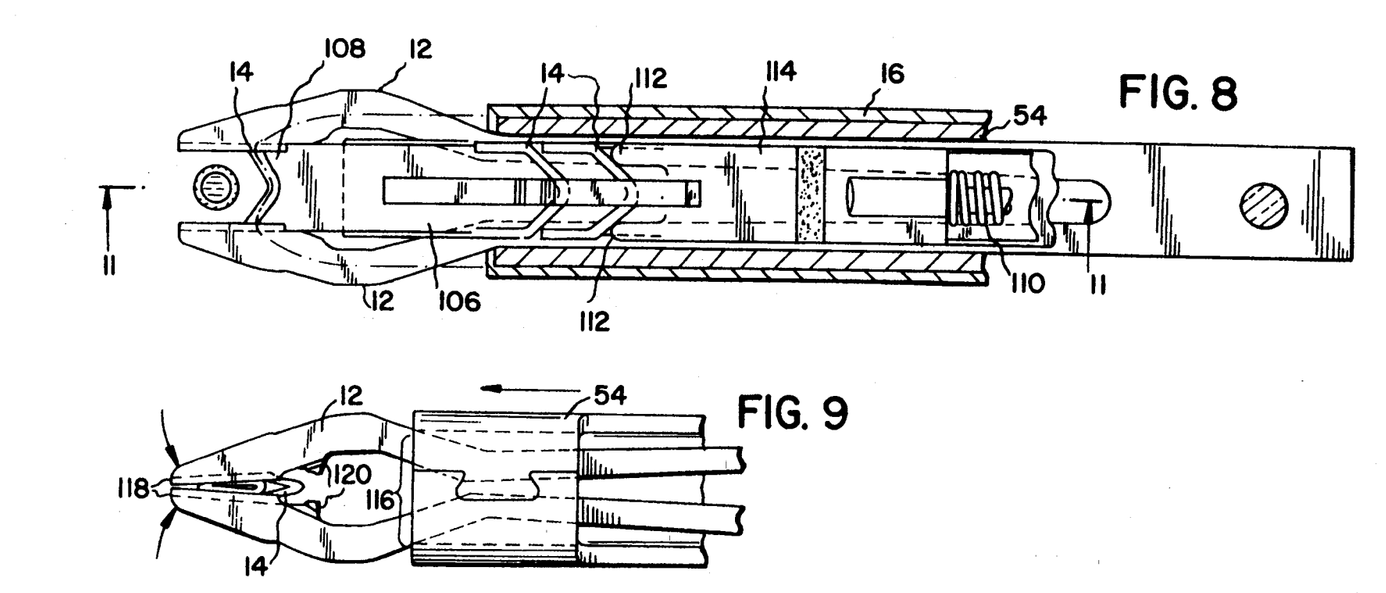
FIG. 8 is a view similar to that of FIG. 6, but of the jaws of the invention as held in FIG. 1.
FIG. 9 is a view of the jaws when held in the clamping position of FIG. 3.

As better seen in FIGS. 6, 7 and 8, the functions of the body portion 20 of the device 10 will now be better described. As seen in FIG. 6, the clip applier 10 is in the fully loaded position and ready for clip closure. The distal and proximal levers 32, 34 are at their clip loading position, and a clip 14 has been loaded within the jaws 12. The user will now squeeze the ring handles 24 one toward the other. In this way, each of the handles 24 will pivot around pivoting post 26 to which each of the ring handles 24 is connected. When this occurs, the distal and proximal levers 32, 34 will be caused to move in opposite directions. This is better seen when comparing the distal and proximal levers 32, 34 as in FIG. 6, with the distal and proximal levers 32, 34 as seen in FIG. 7.

When the ring handles are squeezed together, the distal levers 32 are caused to move to their rotated position, so that they become generally parallel to the shaft 16 of the device. In this way, the clip closing member 48 is caused to move distally, and with it, the clip closing channel 54. This can be seen by comparing the clip closing member 48 as identified in FIG. 6 with the clip closing member as identified in FIG. 7. This distal movement causes clip clamping, as will later be explained.

In addition, when the ring handles 24 are squeezed together, the proximal levers 34 are caused to move about pins 30 so that the slots 51 of the proximal levers 34 move proximally within body 22. This proximal motion causes hook 49 and, consequently, clip feeding member 60 to move in a proximal direction, and causes the timing members 70, 78 as seen in FIGS. 4 and 5 to move as explained above. Now, the spring 40 is also caused to move to a fully stretched position. It is to be noted that spring 40 actually stretches in both distal and proximal directions, enabling smoother stretching and a more compact area in which to stretch the spring 40. (This will ultimately cause the clip closing and clip feeding members 48, 60 to move one toward the other so that the device 10 is recycled. It is during this recycling that another clip 14 is loaded between the pair of jaws 12.)

It is to be noted that, in contrast to some of those devices cited in the Background of the Invention, motion of clip feed member 60 to its proximal most position is caused without any lost motion during squeezing of the handles 24. This results in a mechanically superior device to those devices which must rely on lost motion to accurately position the feeding mechanism with respect to the jaw closure mechanism.

The forming and feeding motions are accomplished on body 22 by a uniform, symmetrically loaded system consisting of body 22 and nine contact points (posts 26, 28, 30 on each handle 24, posts 46 on either side of member 48 and hook 49 on member 60). This arrangement creates a well-balanced, easy to use, low-friction, non-torquing system, readily capable of user manipulation. Also, this configuration enhances the squeeze the user imparts to the jaw 12, and furthermore lessens the probability of the components twisting with respect to the rest of the tool during squeezing.

As better seen by comparing FIGS. 6 and 7, the clip closing channel 54 has moved (through motion of clip closing bar 48) first to its distalmost position (FIG. 7) wherein the clip is fully closed and then to its proximalmost position (FIG. 6). Simultaneously, the feed bar 106 has moved (through motion of clip feed member 60) initially to its proximalmost position (FIG. 7) and then to its distalmost position (FIG. 6). As seen in FIG. 6, spring 40 is in its relaxed state. In FIG. 7, spring 40 has been placed in tension. As a consequence of timing mechanism 70, 78 moving to the position seen in FIG. 7, thus permits spring 40 to contract, so that the device returns to the position as seen in FIG. 6. This recycles the instrument. At this position, another clip 14 is placed between the jaws 12. The timing mechanism 70,78 is therefore a preferred interlock feature to require complete closure of the jaws 12 (and clip 14 contained therein) before the feed bar 106 and clip closure channel 54 are permitted to be returned by the spring 40 to the unactuated positions. These functions are akin to the clip feeding and forming mechanisms also described in U.S. Pat. No. 5,171,249, herein incorporated by reference.

When the ring handles 24 of the mechanism are in the position as in FIG. 6, the jaws 12 are in their position as seen in FIG. 8. In this fashion, the jaws have a clip 14 accepted therebetween and the clip closing channel 54 is in its fully proximal position. The feed bar 106 is in its distalmost position under the clip loading mechanism as seen in FIG. 8, so that end 108 abuts clip 14. In this fashion, clips are prevented from being doubly loaded within the jaws 12. Also, spring 110 urges magazine bar 114 so that it holds the clips 14 (at arms 112) within magazine 18, ready to load a clip 14 within jaws 12.

Figure 10:
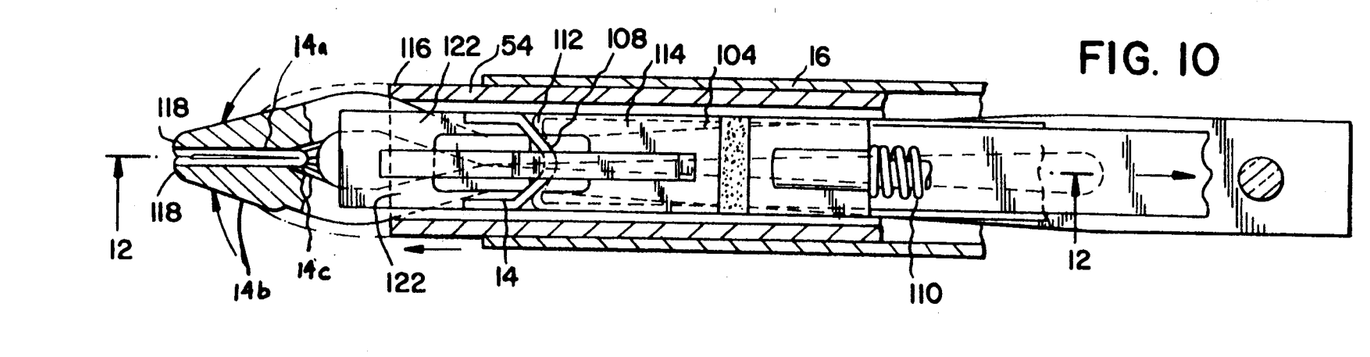
FIG. 10 is a view of the jaws as held in FIG. 9 but showing the jaw closing mechanism.

Now, when the ring handles are moved to the position as in FIG. 7, the clip closing channel 54 moves to its forwardmost position as seen in FIGS. 9 and then to the position of FIG. 10. Thus, the clip 14 is closed between the jaws 12, as channel 116 urges the jaws closed. Uniquely, the clip closing mechanism of this invention is capable of closing the jaws so that the distal ends 118 of the jaws contact one another first. This is seen in FIG. 9. Then, as the clip closing channel 54 moves distally (as seen in FIG. 10), the jaws are urged together by channel 116, so that the crown of the clip abuts the proximal ends 120 of the jaws 12. In fact, proximal ends 122 of each of the jaws actually bend toward one another, much like cantilevered beam members. In this fashion there is virtually parallel closure of the clip legs (14a, 14b of FIG. 10) held within the jaws 12. Thus, occlusion at the apex 146 of the clip is accomplished, due to an overcamming of the clip jaws 14a, 14b. Contact is made at the "knees" 12a of each of the jaws, to prevent over rolling of jaws 12 on each other during camming, and possible opening apart of the clip legs. Because a force is concentrated on the apex or crown 146 of the clips by each of the jaws 12, the additional apex stress prevents apex springback, and creates small (virtually no) clip gaps at the apex. Thus, the clip closing mechanism 54 is capable of achieving more positive closure of the clip and therefore, more secure occluding of the tissue.

Figure 12:
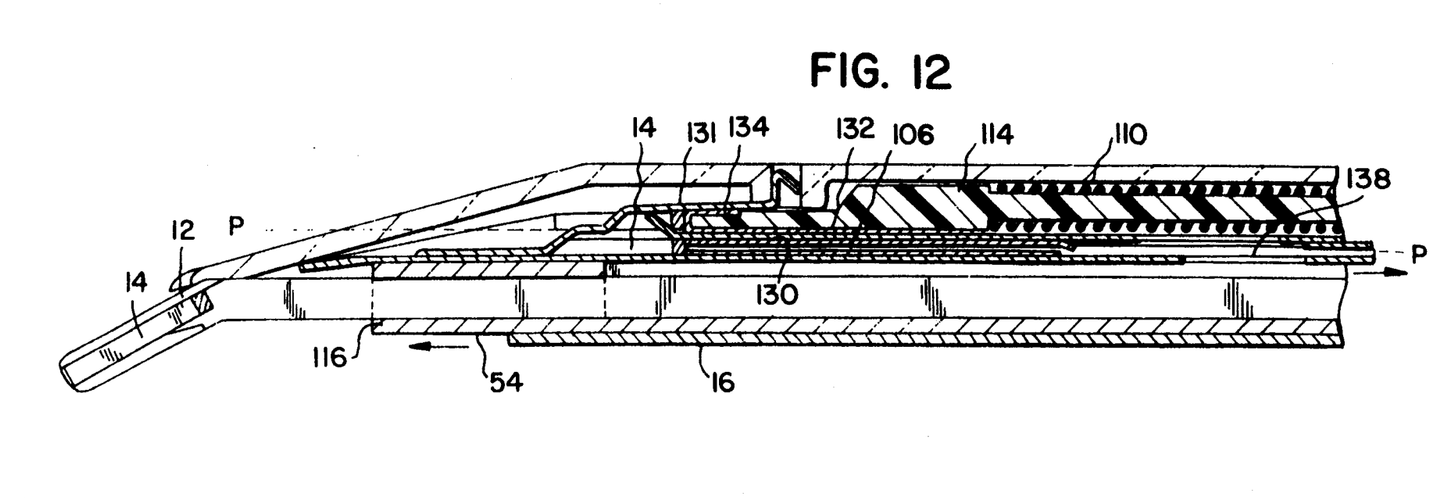
FIG. 12 is a view of the clip closing and feeding mechanism similar to that of FIG. 11, but taken across line 12—12 of FIG. 10.

When the clip closing channel 54 is moved to its proximal position, the feed bar 106 is moved to its forwardmost position, as in FIG. 12. This causes a clip 14 to be placed between the jaws 12. When feed bar 106 returns to its proximal position, a clip from the clip magazine 18 is guided by distal force from the spring 110 contained in the magazine 18 to a position in front of clip feed bar 106, so that this clip 14 is ready to be fed between the jaws 12. Leaf spring 130 operates to prevent double loading of clips, and leaf spring 131 helps load these clips. In this fashion, the clip feeding mechanism accomplishes the same clip feeding functions as in U.S. Pat. No. 5,171,249 incorporated by reference above.

Figure 11:
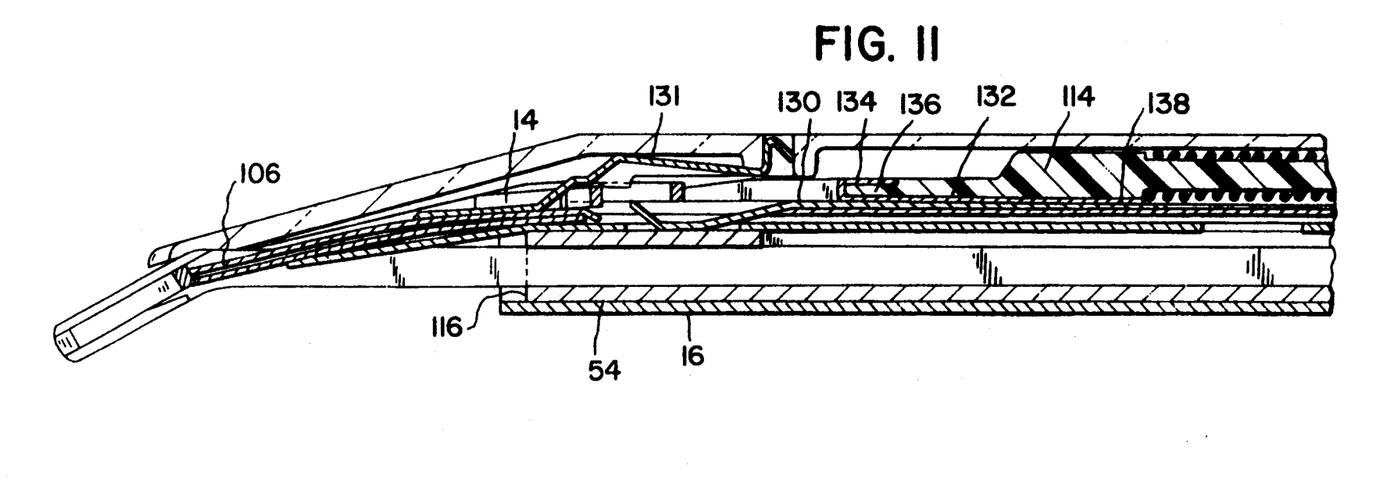
FIG. 11 is a cross-sectional view of the clip feeding mechanism of the invention taken across line 11—11 of FIG. 8.

However, uniquely to this invention, it will be seen from FIGS. 11 and 12 that the clips 14 of this device are stored in magazine 18, on the opposite side of the feed bar 106. That is, the clips in magazine 18 are stored on the opposite side of the plane of feed bar 106, as compared to jaws 12, as seen in FIG. 11. The clips 14 are loaded into the jaws 12, and the jaws 12 curve away from the plane of the feed bar 106 (or more correctly, shaft 16) so that they are more fully exposed to the field of vision of the user. Thus, because the clips 14 are stored on the opposite of this plane P, they are more readily visible. In this fashion, the clips 14 can be seen throughout the clip clamping procedure, and thus the vessel being acted upon is more properly occluded. Also, because the clip 14 held between jaws 12, is very close to being in the plane of the closing mechanism 116 which cams jaws 12 together, there is very little roll of the jaws and clip during forming, in contrast to prior art devices. Of course, this reduced twisting is a great benefit, because it allows greater closing force to be applied directly to the clip crown, so that the jaws of the clip can remain relatively thin, and yet, produce the desired forces.

The invention disclosed herein also contains a lockout member, as better seen in FIGS. 11 and 12. This lockout member 132 contains hook 134 attached to spur 136 of magazine bar 114, and proximal end 138, cammed into position by leaf spring 130. Once the last of the clips has been fired and magazine bar 114 is fully distal in the shaft 16, proximal end 138 drops in front of holes contained in spring 130 and feed bar 106, so that proximal end 138 blocks the path of feed bar 106. Thus, this "sensory"-type lockout member 132 blocks feed bar 106, and lockout member 132 is held in shear. The metal lockout member 132 withstands shear quite reliably. It has been found that this type of lockout is more readily and securely accomplished.

In conjunction with the lockout as in FIG. 11 and 12 there is provided a lockout as in FIG. 4. This occurs when the last of the clips has been fired. Lockout spring 140 is attached to body 22 at hook 142. Spring 140 mates with cam edge 146 on clip feed member 60, on side 144. Cam 146 causes tip 148 to be cammed out of the path of motion of clip closing bar 48, during every cycling of the instrument. However, once lockout member 132 is dropped in place (as described above and in conjunction with FIGS. 11 and 12) clip feed member 60 is prevented from moving distally. In this fashion, edge 146 does not contact side 144. For this reason, tip 148 will rest in hook-shaped lock 150 on clip closing bar 48 after the ring handles 24 are opened, and prevent the next attempted actuation. Thus, a second backup lockout is obtained. This unique double lockout system provides for redundant lockout and of course, creates a more reliable mechanism. It is believed that this enhanced safety mechanism causes a more reliable device with regard to lockout.

Thus, this invention has been described in connection with a particularly preferred embodiment. It is to be realized that the claims appended hereto will more accurately describe this invention as well, as their equivalents.

What is claimed is:

1. A ligating clip applier comprising:

a pair of jaws each said jaw with a proximal end and a distal end;

a jaw closure mechanism carried by a shaft, said jaw closure mechanism useful for closing said jaws;

a stack of clips disposed on said shaft, at least one clip from said stack contained between said jaws, said clips each having a pair of legs containing proximal ends and said legs angularly attached to one another at said proximal ends;

wherein said jaw closure mechanism causes said jaws to contact said clip first distally and then proximally, such that said jaws are parallel during at least one position during closure, and such that said leg proximal ends contact one another so that the angle included therebetween is substantially 0°;

said jaw closure mechanism containing a longitudinally reciprocable bar capable of moving along a path and feeding a said clip into said jaws;

a handle attached to said shaft mechanism for operating said jaw closure mechanism; and a lockout mechanism held in place one said shaft by said stack of clips and comprising a leaf spring, said leaf spring activated after closing of the last of said clips to move into said path and across said path, said leaf spring blocking movement of said longitudinally reciprocating bar.

2. The applier of claim 1 wherein said jaws are contained in a jaw assembly, and said jaw assembly connecting said jaws to a handle assembly, said jaw assembly containing a shaft attached to a pair of jaws, said shaft defining a longitudinal axis in a first plane and said jaws defining an axis placed at an angle to said longitudinal axis; and     a clip magazine located on said shaft and containing a plurality of clips capable of being loaded into said jaws, said magazine placed on one side of said first plane and said jaws placed on the opposite side of said plane.

3. The applier of claim 2 wherein said jaws angle away from said first plane at an angle of about 30°.

4. The applier of claim 2 wherein said clip magazine is contained in a plane immediately adjacent said first plane.

5. The clip applier of claim 1 wherein said jaw closure mechanism causes said jaw proximal ends to become closer to one another then said jaw distal ends during at least one position during closure.

6. The applier of claim 1 wherein said lockout mechanism is a first lockout mechanism and said applier further comprising a second lockout mechanism connected to said shaft and activated by activation of said first lockout mechanism.

7. The applier of claim 6 wherein said second lockout mechanism is a leaf spring opposing said reciprocating bar.

8. A ligating clip applier containing:

a clip carrying channel having a plurality of clips;

a pair of jaws extending from said channel for closing a clip from said plurality of clips, and said applier thereafter allowing said clip closed between said jaws to be expelled from said applier and capable of having a clip loaded therebetween from said clip carrying channels;

a jaw closure mechanism contained on a shaft, said shaft proximally attached to said jaws for closing said jaws, said jaw closure mechanism containing a longitudinally reciprocating bar capable of moving along a path and feeding a clip within said jaws;

a handle mechanism proximally attached to said shaft for operating said jaw closure mechanism; and   a lockout mechanism held in place by said clip carrying channel and comprising a leaf spring, said leaf spring activated after closing of the last of said clips to move into said path and across said path, said leaf spring blocking movement of said longitudinally reciprocating bar and wherein said lockout mechanism is a first lockout mechanism and said applier further comprising a second lockout mechanism connected to said clip carrying channel and activated by activation of said first lockout mechanism.

9. The applier of claim 8 wherein said reciprocating bar defines a first plane and further comprising said jaws defining an axis placed at an angle transverse said longitudinal axis; and     a clip magazine containing a plurality of clips capable of being loaded in said jaws, said magazine placed on one side of said first plane and said jaws placed on the opposite side of said plane.

10. The applier of claim 9 wherein said jaws angle away from said first plane at an angle of about 30°.

11. The applier of claim 9 wherein said clip magazine is contained in a plane immediately adjacent said first plane.

12. The applier of claim 8 further comprising a jaw closure mechanism wherein said jaw closure mechanism causes said jaws to contact clip first distally and then proximally, such that said jaws are parallel during at least one position during closure, and such that such leg proximal ends contact one another so that the angle included therebetween is substantially 0°.

13. The clip applier of claim 12 wherein said jaw closure mechanism causes said jaw proximal ends to become closer to one another then said jaw distal ends during at least one position during closure.

14. The applier of claim 8 wherein said second lockout mechanism is a leaf spring opposing said reciprocating bar.

15. A ligating clip applier comprising:

an elongate support shaft and a magazine of clips contained in said shaft;

a pair of jaws mounted in, and extending from, said support shaft for receiving and closing one of said clips;

a handle assembly carrying said shaft and having a body and at least one handle pivotably mounted to said body;

a clip feeding mechanism movable relative to said shaft and handle assembly between an extended position to feed said clip into said jaws and a retracted position for receiving another clip from said magazine;

a jaw closure mechanism connected to said handle for movement relative to said shaft and handle assembly between an extended position engaging and closing said jaws and a retracted position permitting said jaws to open;

a tension spring connected between said clip feeding mechanism and said jaw closure mechanism with each end of said spring movable relative to said body whereby said spring biases said jaw closure mechanism to said retracted position and said clip feeding mechanism to said extended position; and   a link pivotably connected at one end at a fixed location on said handle and at the other end at a fixed location on said clip feeding mechanism for movement relative to said handle and said clip feeding mechanism while the pivot connections at each end of said link remain free of lateral guide surfaces whereby pivoting said handle effects retraction of said clip feeding mechanism and simultaneous extension of said jaw closure mechanism.

16. The applier of claim 15 wherein said jaws are contained in a jaw assembly, and said jaw assembly connecting said jaws to a handle assembly, said jaw assembly containing a shaft attached to a pair of jaws, said shaft defining a longitudinal axis in a first plane and said jaws defining an axis placed at an angle to said longitudinal axis; and     a clip magazine containing a plurality of clips capable of being loaded into said jaws, said magazine placed on one side of said first plane and said jaws placed on the opposite side of said plane.

17. A ligating clip applier comprising:

an elongate support shaft and a magazine of clips contained in said shaft;

a pair of jaws mounted in, and extending from, said support shaft for receiving and closing one of said clips;

a handle assembly carrying said shaft and having a body and at least one handle pivotably mounted to said body;

a clip feeding mechanism movable relative to said shaft and handle assembly between an extended position to feed said clip into said jaws and a retracted position for receiving another clip from said magazine;

a jaw closure mechanism movable relative to said shaft and handle assembly between an extended position engaging and closing said jaws and a retracted position permitting said jaws to open;

a tension spring connected between said clip feeding mechanism and said jaw closure mechanism with each end of said spring movable relative to said body whereby said spring biases said jaw closure mechanism to said retracted position and said clip feeding mechanism to said extended position;

a first link pivotably connected at one end at a fixed location on said handle and at the other end at a fixed location on said jaw closure mechanism for movement relative to said handle and said jaw closure mechanism; and a second link pivotably connected at one end at a fixed location on said handle and at the other end at a fixed location on said clip feeding mechanism for movement relative to said handle and said clip feeding mechanism whereby closing said handle effects retraction of said clip feeding mechanism and simultaneous extension of said jaw closure mechanism.

18. A ligating clip applier comprising:

an elongate support shaft and a magazine of clips contained in said shaft;

a pair of jaws mounted in, and extending from, said support shaft for receiving and closing one of said clips;

a handle assembly carrying said shaft and having a body and at least one handle pivotably mounted to said body;

a clip feeding mechanism movable relative to said shaft and handle assembly between an extended position to feed said clip into said jaws and a retracted position for receiving another clip from said magazine;

a jaw closure mechanism movable relative to said shaft and handle assembly between an extended position engaging and closing said jaws and a retracted position permitting said jaws to open;

a tension spring connected between said clip feeding mechanism and said jaw closure mechanism with each end of said spring movable relative to said body whereby said spring biases said jaw closure mechanism to said retracted position and said clip feeding mechanism to said extended position;

a first link pivotably connected at one end at a fixed location on said handle and at the other end at a fixed location on said jaw closure mechanism for movement relative to said handle and said jaw closure mechanism; and a second link pivotable connected at one end at a fixed location on said handle and at the other end at a fixed location on said clip feeding mechanism for movement relative to said handle and said clip feeding mechanism while the pivot connections at each end of said second link remain free of lateral guide surfaces whereby closing said handle effects retraction of said clip feeding mechanism and simultaneous extension of said jaw closure mechanism.

* * * * *